(12) United States Patent
Matsuki et al.

(10) Patent No.: US 7,718,228 B2
(45) Date of Patent: May 18, 2010

(54) COMPOSITION FOR FORMING SILICON-COBALT FILM, SILICON-COBALT FILM AND METHOD FOR FORMING SAME

(75) Inventors: Yasuo Matsuki, Tokyo (JP); Daohai Wang, Tokyo (JP); Tatsuya Sakai, Tokyo (JP); Haruo Iwasawa, Tokyo (JP)

(73) Assignee: JSR Corporation, Tokyo (JP)

( * ) Notice: Subject to any disclaimer, the term of this patent is extended or adjusted under 35 U.S.C. 154(b) by 1046 days.

(21) Appl. No.: 10/575,478

(22) PCT Filed: Oct. 6, 2004

(86) PCT No.: PCT/JP2004/015101

§ 371 (c)(1),
(2), (4) Date: Apr. 12, 2006

(87) PCT Pub. No.: WO2005/038891

PCT Pub. Date: Apr. 28, 2005

(65) Prior Publication Data

US 2007/0077742 A1    Apr. 5, 2007

(30) Foreign Application Priority Data

Oct. 16, 2003    (JP) .............................. 2003-356158

(51) Int. Cl.
*B05D 3/02* (2006.01)
(52) U.S. Cl. ............... 427/376.1; 427/376.3; 427/376.6
(58) Field of Classification Search .............. 427/376.1, 427/376.3, 376.6
See application file for complete search history.

(56) References Cited

U.S. PATENT DOCUMENTS

| 5,700,400 | A | * | 12/1997 | Ikai et al. .................... 252/513 |
| 6,251,777 | B1 | * | 6/2001 | Jeng et al. ................... 438/682 |
| 6,737,324 | B2 | * | 5/2004 | Chang ........................ 438/300 |
| 2002/0038889 | A1 | * | 4/2002 | Yamazaki et al. ........... 257/347 |
| 2002/0086486 | A1 | * | 7/2002 | Tanaka et al. ............... 438/300 |

FOREIGN PATENT DOCUMENTS

| JP | 53-60171 | 5/1978 |
| JP | 4-53132 | 2/1992 |
| JP | 4-53512 | 2/1992 |
| JP | 3382743 | 12/2002 |
| WO | 99/22411 | 5/1999 |
| WO | 00/59040 | 10/2000 |

OTHER PUBLICATIONS

Sadoh, Taizoh et al., "High-Performance MOS Tunneling Cathode with $CoSi_2$ Gate Electrode", Jpn. J. Appl. Phys., vol. 40, Part 1, No. 4B, pp. 2775-2778, 2001.
Zaima, Shigeaki et al., "Formation of silicide at metal/silicon interface and low-resistivity contacts", Applied Physics, vol. 63, No. 11, pp. 1093-1105, 1994. (with English abstract).

* cited by examiner

*Primary Examiner*—Shamim Ahmed
(74) *Attorney, Agent, or Firm*—Oblon, Spivak, McClelland, Maier & Neustadt, L.L.P.

(57) ABSTRACT

There are provided a composition and method for forming a silicon-cobalt film at low production cost without expensive vacuum equipment and high-frequency generator. The composition is a silicon-cobalt film forming composition comprising a silicon compound and a cobalt compound. A silicon-cobalt film is formed by applying this composition on a substrate and subjecting the resulting substrate to a heat treatment and/or a light treatment.

20 Claims, 1 Drawing Sheet

COMPOSITION FOR FORMING SILICON-COBALT FILM, SILICON-COBALT FILM AND METHOD FOR FORMING SAME

This application is a 371 of PCT/JP04/15101 filed Oct. 6, 2004.

TECHNICAL FIELD

The present invention relates to a silicon-cobalt film, a method for forming the film, and a composition for forming the film. More specifically, it relates to production of MOS-type semiconductor device, particularly to a silicon-cobalt film forming composition which is useful in production of semiconductor device having silicide gate electrodes and a silicide source-drain region, a silicon-cobalt film, and a method for forming the film.

BACKGROUND ART

Along with an increase in integration of semiconductor devices and an increase in fineness of patterns, a reduction in the resistance of a gate electrode has been desired. As a method for reducing the resistance of the gate electrode, a method of turning the gate electrode into a silicide by a SALICIDE (Self-Aligned Silicide) technique is known.

To form an ohmic contact by the work function of the interface between a metallic material for wiring and silicon in a silicon semiconductor, a method of modifying the surface of the silicon layer with other metal such as Co, Ni, Au, Ag, Ti, Pd or Al and a silicide or the like has been often used. Further, as the silicide, cobalt silicide has been often used in view of the specific resistance of the silicide itself and matching between the lattice parameters of the silicide and silicon (refer to U.S. Pat. No. 3,382,743).

These silicides are generally formed by a method comprising laminating a metal film such as Co, Ni, Au, Ag, Ti, Pd or Al on a silicon film by a vacuum process such as a vacuum deposition process, a sputtering process, a plasma CVD (Chemical Vapor Deposition) process, a thermal CVD process, an optical CVD process or an MOCVD (Metal Organic CVD) process and then treating the resulting film at high temperatures (refer to Jpn. J. Appl. Phys. Vol. 40, pp. 2,778 (2001) and Applied Physics, vol. 63, No. 11, pp. 1,093 (1994)).

However, these deposition methods have the following problems. That is, since they deposit silicon and cobalt in a gas phase regardless of physical deposition or chemical deposition, production costs are high due to a large-size apparatus, and it is difficult to form a coating film on a large-area substrate because particles and oxides are liable to be produced.

Further, since the deposition methods use a compound which becomes gaseous under vacuum regardless of physical deposition or chemical deposition, compounds that can be used as a raw material are limited, and highly sealed vacuum equipment is required. These also cause an increase in production costs.

Meanwhile, in various electric circuits, resistors are used for the purposes of voltage drop, voltage division and generation of module heat. In general, a number of resistors having various electric resistance values must be used according to their purposes, installation positions and the like. Therefore, electric circuits having such resistors cannot help having a certain size, thereby inhibiting a reduction in the size of electric equipment.

It is obvious that if a certain electric resistance can be imparted to a wiring material, many resistors in the circuit become unnecessary, thereby contributing to a reduction in the size of electric equipment. Although a silicon-cobalt alloy (cobalt silicide) is expected to be promising as such a wiring material, its formation requires a large-size apparatus as described above and therefore causes high costs. Hence, its use in this field has hardly been studied.

Under the above circumstances, an industrial film formation method of a silicon-cobalt film which requires no expensive vacuum equipment and high-frequency generator and does not require high production costs has been strongly desired.

DISCLOSURE OF THE INVENTION

The present invention has been conceived in view of the above circumstances, and an object of the present invention is to provide a composition for forming a silicon-cobalt film easily at low production costs without expensive vacuum equipment and high-frequency generator, a method for forming a silicon-cobalt film by use of the composition, and a silicon-cobalt film formed by the method.

According to the present invention, firstly, the above object of the present invention is achieved by a silicon-cobalt film forming composition containing a silicon compound and a cobalt compound.

Further, secondly, the above object of the present invention is achieved by a method for forming a silicon-cobalt film which comprises forming a coating film of the above silicon-cobalt film forming composition on a substrate and subjecting the film to a heat treatment and/or a light treatment.

Further, thirdly, the above object of the present invention is achieved by a silicon-cobalt film formed by the above method.

BEST MODE FOR CARRYING OUT THE INVENTION

Figure 1:
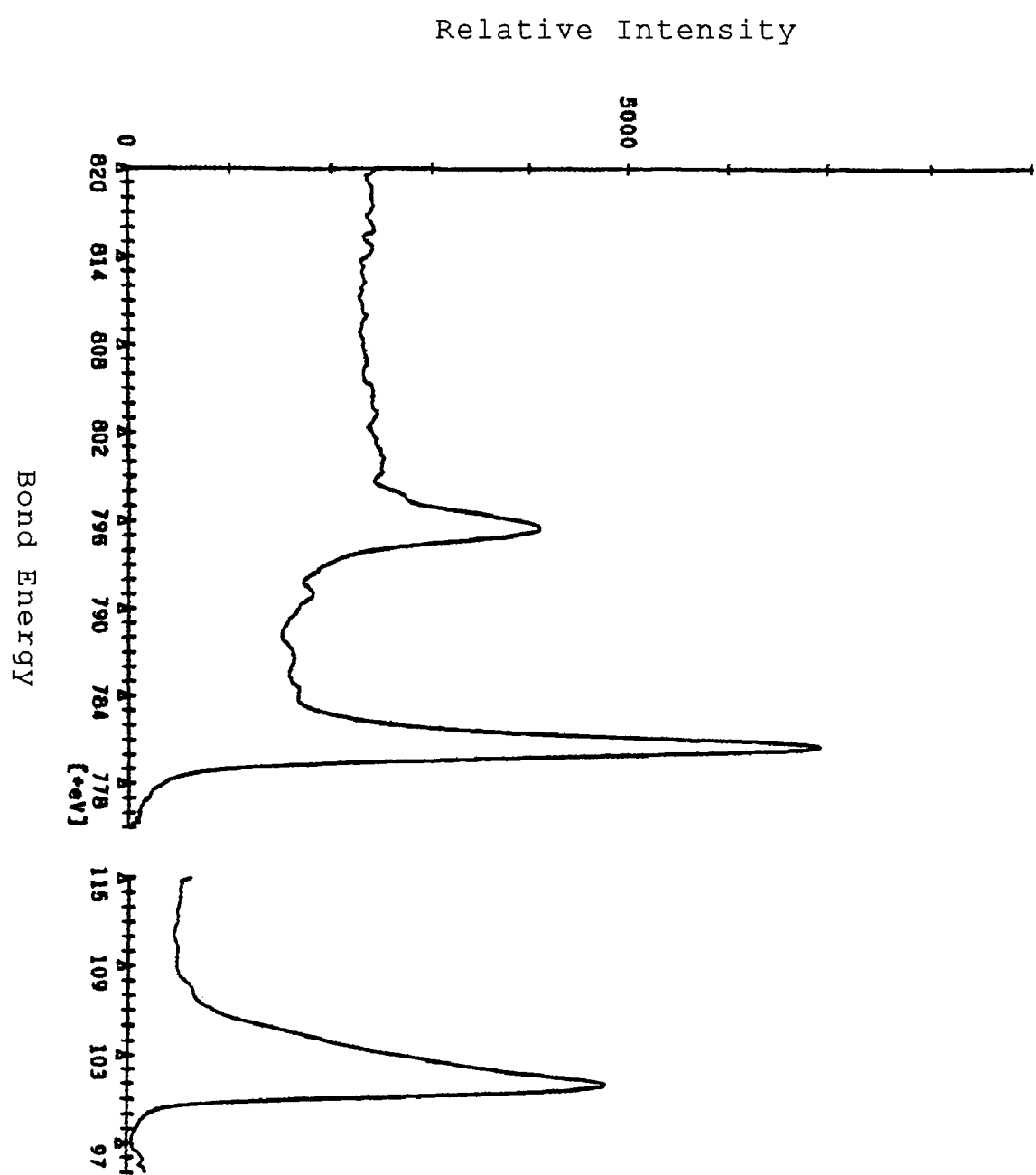
FIG. 1 is an ESCA spectrum of a silicon-cobalt film obtained in Example 1.

Hereinafter, the present invention will be further described.

Silicon-Cobalt Film Forming Composition

The silicon-cobalt film forming composition of the present invention contains a silicon compound and a cobalt compound.

The type of the silicon compound contained in the silicon-cobalt film forming composition of the present invention is not particularly limited as long as the object of the present invention can be achieved. For example, in the above silicon-cobalt film forming composition, the above silicon compound is at least one compound selected from the group consisting of compounds represented by the following formulae (1a) to (1d):

$$Si_i X_{2i+2} \tag{1a}$$

(wherein X is a hydrogen atom, a halogen atom or a monovalent organic group, and i is an integer of 2 or larger ($i \geq 2$)), $$Si_j X_{2j} \tag{1b}$$

(wherein X is a hydrogen atom, a halogen atom or a monovalent organic group, and j is an integer of 3 or larger ($j \geq 3$)), $$Si_m X_{2m-2} \tag{1c}$$

(wherein X is a hydrogen atom, a halogen atom or a monovalent organic group, and m is an integer of 4 or larger (m≧4)), $$Si_k X_k \quad (1d)$$

(wherein X is a hydrogen atom, a halogen atom or a monovalent organic group, and k is 6, 8 or 10).

Illustrative examples of the monovalent organic group represented by X in the formulae (1a), (1b), (1c) and (1d) include an alkyl group having 1 to 12 carbon atoms, an alkenyl group having 2 to 12 carbon atoms, an alkynyl group having 2 to 12 carbon atoms, and an aromatic group having 6 to 12 carbon atoms.

Illustrative examples of the halogen atom include a chlorine atom and a bromine atom.

In the above formulae (1a), (1b), (1c) and (1d), X is preferably a hydrogen atom or a halogen atom, more preferably a hydrogen atom.

In the above formula (1a), i is preferably 2 to 10. In the above formula (1b), j is preferably 3 to 10. In the above formula (1c), m is preferably 4 to 13.

An example of the compound represented by the above formula (1a) is a chain silane compound. An example of the compound represented by the above formula (1b) is a cyclic silane compound. An example of the compound represented by the above formula (1c) is a silane compound having a spiro structure. An example of the compound represented by the above formula (1d) is a basket-shaped silane compound. Of these, the chain silane compound and the cyclic silane compound are preferred, and the cyclic silane compound is more preferred.

Specific examples of the chain silane compound include n-pentasilane, iso-pentasilane, neo-pentasilane, n-hexasilane, n-heptasilane, n-octasilane, n-nonasilane, tetrachlorosilane, tetrabromosilane, hexachlorodisilane, hexabromodisilane, octachlorotrisilane and octabromotrisilane. Specific examples of the cyclic silane compound include cyclotrisilane, cyclotetrasilane, cyclopentasilane, silylcyclotetrasilane, silylcyclotrisilane, silylcyclopentasilane, cyclohexasilane, heptasilane and cyclooctasilane. Specific examples of the silane compound having a spiro structure include 1,1'-bicyclobutasilane, 1,1'-bicyclopentasilane, 1,1'-bicyclohexasilane, 1,1'-bicycloheptasilane, 1,1'-cyclobutasilylcyclopentasilane, 1,1'-cyclobutasilylcyclohexasilane, 1,1'-cyclobutasilylcycloheptasilane, 1,1'-cyclopentasilylcyclohexasilylsilane, 1,1'-cyclopentasilylcycloheptasilane, 1,1'-cyclohexasilylcycloheptasilane, spiro[2.2]pentasilane, spiro[3.3]heptasilane, spiro[4.4]nonasilane, spiro[4.5]decasilane, spiro[4.6]undecasilane, spiro[5.5]undecasilane, spiro[5.6]undecasilane and spiro[6.6]tridecasilane. Specific examples of the basket-shaped silane compound include hexasilaprismane and octasilacubane.

Of these specific examples, particularly preferred specific examples are cyclopentasilane, silylcyclopentasilane, cyclotetrasilane, silylcyclotetrasilane, cyclotrisilane and silylcyclotrisilane.

The above silicon compounds are used alone or in combination of two or more.

The type of the cobalt compound contained in the silicon-cobalt film forming composition of the present invention is not particularly limited as long as the object of the present invention can be achieved.

A Co complex having at least either one of a CO ligand or a ligand of π coordination is preferably used.

Illustrative examples of the Co complex include a compound represented by the following formula (2):

$$L^1_c Co(CO)_d Y_e \quad (2)$$

wherein $L^1$ is a ligand selected from a group represented by the following formula (2)-1:

$$(CH_3)_n Cp \quad (2)\text{-}1$$

wherein Cp is a $\eta^5$-cyclopentadienyl group, and n is an integer of 0 to 5, an indenyl group, 1,3-cyclooctadiene, 1,4-cyclooctadiene, 1,5-cyclooctadiene, 1,3-butadiene, norbornadiene and allyl, Y is a halogen atom, a hydrogen atom, a methyl group or an ethyl group, c is 1 or 2, d is 0, 1, 2 or 4, e is 0 or 2, and c+d+e is 2, 3, 4 or 5, provided that when c is 2, two $L^1$s may be the same or different, a compound represented by the following formula (3):

$$L^2_f Co_2(CO)_g R_h \quad (3)$$

wherein $L^2$ is defined by the above formula (2)-1 or is a ligand selected from 1,3-cyclohexadiene, 1,4-cyclohexadiene, allyl, norbornadiene and cyclooctene, R is a halogen atom, PhC:::CPh (wherein ::: represents a triple bond), CCH₃, CH₃, CH₂, CH or CPh, f is 0, 1, 2 or 4, g is 1, 2, 4, 6 or 8, h is 0, 1 or 2, and f+g+h is 4, 6, 7 or 8, a compound represented by the following formula (4):

$$Co_3(CO)_9 CZ \quad (4)$$

wherein Z is a halogen atom, a compound represented by the following formula (5):

$$Co_3(CO)_{12} \quad (5), \text{ and}$$

a compound represented by the following formula (6):

$$Co_4(CO)_{12} \quad (6).$$

Specific examples of the complex represented by the formula (2) include cyclopentadienyl dicarbonyl cobalt, cyclopentadienyl carbonyl cobalt difluoride, cyclopentadienyl carbonyl cobalt dichloride, cyclopentadienyl carbonyl cobalt dibromide, cyclopentadienyl carbonyl cobalt diiodide, bis(cyclopentadienyl)cobalt, bis(cyclopentadienyl)carbonyl cobalt, bis(cyclopentadienyl)dicarbonyl cobalt, methyl cyclopentadienyl dicarbonyl cobalt, methyl cyclopentadienyl carbonyl cobalt difluoride, methyl cyclopentadienyl carbonyl cobalt dichloride, methyl cyclopentadienyl carbonyl cobalt dibromide, methyl cyclopentadienyl carbonyl cobalt diiodide, bis(methyl cyclopentadienyl)cobalt, bis(methyl cyclopentadienyl)carbonyl cobalt, bis(methyl cyclopentadienyl) dicarbonyl cobalt, tetramethyl cyclopentadienyl dicarbonyl cobalt, tetramethyl cyclopentadienyl carbonyl cobalt difluoride, tetramethyl cyclopentadienyl carbonyl cobalt dichloride, tetramethyl cyclopentadienyl carbonyl cobalt dibromide, tetramethyl cyclopentadienyl carbonyl cobalt diiodide, bis(tetramethyl cyclopentadienyl)cobalt, bis(tetramethyl cyclopentadienyl)carbonyl cobalt, bis(tetramethyl cyclopentadienyl)dicarbonyl cobalt, 1,5-cyclooctadiene dicarbonyl cobalt, 1,5-cyclooctadiene carbonyl cobalt difluoride, 1,5-cyclooctadiene carbonyl cobalt dichloride, 1,5-cyclooctadiene carbonyl cobalt dibromide, 1,5-cyclooctadiene carbonyl cobalt diiodide, bis(1,5-cyclooctadiene)cobalt, bis(1,5-cyclooctadiene)carbonyl cobalt, 1,3-cyclooctadiene dicarbonyl cobalt, 1,3-cyclooctadiene carbonyl cobalt difluoride, 1,3-cyclooctadiene carbonyl cobalt dichloride, 1,3-cyclooctadiene carbonyl cobalt dibromide, 1,3-cyclooctadiene carbonyl cobalt diiodide, bis(1,3-cyclooctadiene)cobalt, bis(1,3-cyclooctadiene)carbonyl cobalt, indenyl dicarbonyl cobalt, indenyl carbonyl cobalt difluoride, indenyl carbonyl cobalt dichloride, indenyl carbonyl cobalt dibromide, indenyl carbonyl cobalt diiodide, bis(indenyl)cobalt, bis(indenyl)carbonyl cobalt, $\eta^3$-allyl tricarbonyl cobalt, $\eta^3$-allyl carbonyl cobalt difluoride, $\eta^3$-allyl carbonyl cobalt dichloride, $\eta^3$-allyl carbonyl cobalt dibromide, $\eta^3$-allyl carbonyl cobalt diiodide, bis($\eta^3$-allyl)carbonyl cobalt, cyclopentadienyl(1,5-cyclooctadiene)cobalt, cyclopentadienyl(tetramethyl cyclopentadienyl) cobalt, tetramethyl cyclopentadienyl(1,5-cyclooctadiene)cobalt, cyclopentadienyl(methyl cyclopentadienyl)cobalt, methyl cyclopentadienyl(tetramethyl cyclopentadienyl)cobalt, methyl cyclopentadienyl(1,5-cyclooctadiene)cobalt, cyclopentadienyl(1,3-cyclooctadiene)cobalt, tetramethyl cyclopentadienyl(1,3-cyclooctadiene)cobalt, methyl cyclopentadienyl(1,3-cyclooctadiene)cobalt, cyclopentadienyl(cyclooctatetraenyl)cobalt, cyclopentadienyl(1,3-butadiene)cobalt, cyclopentadienyl(norbornadiene) cobalt, tetracarbonyl cobalt hydride, cyclopentadienyl carbonyl cobalt dihydride, methyl cyclopentadienyl carbonyl cobalt dihydride, tetramethyl cyclopentadienyl carbonyl cobalt dihydride, methyl tetracarbonyl cobalt, and ethyl tetracarbonyl cobalt.

Further, specific examples of the complex represented by the above formula (3) include bis(cyclopentadienyl)dicarbonyl cobalt, bis(tetramethyl cyclopentadienyl)dicarbonyl dicobalt, octacarbonyl dicobalt, (norbornene)hexacarbonyl dicobalt, cyclooctene hexacarbonyl dicobalt, bis(cyclopentadienyl)dimethyl dicarbonyl dicobalt, tetra($\eta^3$-allyl)dicobalt diiodide, bis(1,3-cyclohexadienyl)tetracarbonyl dicobalt, bis(norbornene)tetracarbonyl dicobalt, bis(cyclopentadienyl)dicarbonyl dicobalt, and complexes represented by the following formulae (i) to (v).

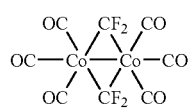
(i)

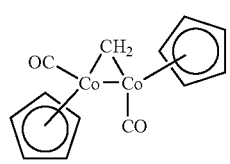
(ii)

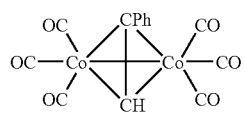
(iii)

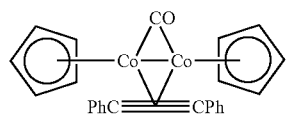
(iv)

-continued

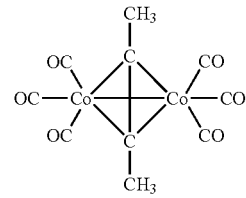
(v)

Specific examples of the complex represented by the above formula (4) include a complex represented by the following formula (vi).

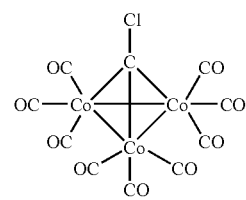
(vi)

Of these, preferred complexes are bis(cyclopentadienyl) cobalt, bis(tetracyclopentadienyl)cobalt, bis(1,3-cyclooctadienyl)cobalt, bis(1,5-cyclooctadiene)cobalt, bis(indenyl)cobalt, cyclopentadienyl dicarbonyl cobalt, methyl cyclopentadienyl dicarbonyl cobalt, tetramethyl cyclopentadienyl dicarbonyl cobalt, (1,3-cyclooctadiene)dicarbonyl cobalt, (1,5-cyclooctadiene)dicarbonyl cobalt, indenyl dicarbonyl cobalt, $\eta^3$-allyl tricarbonyl cobalt, cyclopentadienyl(1,3-cyclooctadiene)cobalt, cyclopentadienyl(1,5-cyclooctadiene)cobalt, cyclopentadienyl(indenyl)cobalt, indenyl(1,3-cyclooctadiene)cobalt, indenyl(1,5-cyclooctadiene)cobalt, and octacarbonyl dicobalt.

These cobalt compounds can be used alone or in combination of two or more.

In the silicon-cobalt film forming composition of the present invention, the proportions of the above silicon compound and cobalt compound can be set at appropriate proportions according to applications of the desired silicon-cobalt film as will be described below.

The silicon-cobalt film forming composition of the present invention can contain other components as required, in addition to the above silicon compound and cobalt compound.

Illustrative examples of such other components include metal or semiconductor particles, metal oxide particles, and surfactants.

The above metal or semiconductor particles can be contained to adjust the electric properties of the silicon-cobalt film to be obtained. Specific examples of the particles include gold, silver, copper, aluminum, nickel, iron, niobium, titanium, silicon, indium, and tin. These can be contained alone or in combination of two or more. The particle diameter of the metal or semiconductor particles is preferably about 10 to 1,000 nm, for example. The particles may have any shape as exemplified by a disk shape, a cylindrical shape, a polyangular columnar shape or a scale shape, in addition to a nearly spherical shape. The content of the metal or semiconductor particles is preferably 50 wt % or lower ($C_1 \leqq 50$ wt %), more preferably 10 wt % or lower ($C_1 \leqq 10$ wt %), based on the total amount ($C_1$) of the above silicon compound, cobalt compound and metal or semiconductor particles.

The silicon-cobalt film forming composition of the present invention can contain a surfactant for the purposes of improving wettability to a substrate to which the composition is to be applied, improving the surface smoothness of the coating film and preventing the occurrence of spots or orange peel in the coating film.

Illustrative examples of such a surfactant include a fluorine-based surfactant, a silicone-based surfactant and a nonionic surfactant.

Specific examples of the fluorine-based surfactant include EFTOP EF301, EF303 and EF352 (products of Shin Akita Kasei Co., Ltd.), MEGAFAC F171 and F173 (products of DAINIPPON INKAND CHEMICALS, INC.), ASAHI-GUARD AG710 (product of ASAHI GLASS CO., LTD.), FLORAD FC-170C, FC430 and FC431 (products of SUMITOMO 3M Ltd.), SURFLON S-382, SC101, SC102, SC103, SC104, SC105 and SC106 (products of ASAHI GLASS CO., LTD.), BM-1000 and BM-1100 (products of B.M-Chemie Co., Ltd.), and Schsego-Flour (product of Schwegmann Co., Ltd.).

Specific examples of the nonionic surfactant include EMULGEN 105, 430, 810 and 920, RHEODOL SP-40S and TW-L120, EMANOL 3199 and 4110, EXEL P-40S, BRIDGE 30, 52, 72 and 92, ARACEL 20, EMASOL 320, TWEEN 20 and 60 and MARGE 45 (products of Kao Corporation), NONIBOL 55 (product of SANYO KASEI CO., LTD.), CHEMISTAT 2500 (product of Sanyo Chemical Industries, Ltd.), SN-EX9228 (product of SAN NOPCO LTD.), and NONAL 530 (product of TOHO Chemical Industry Co., LTD.).

In the silicon-cobalt film forming composition of the present invention, the content ($C_2$) of the surfactant is preferably 5 wt % or lower ($C_2 \leq 5$ wt %), more preferably 0.1 wt % or lower ($C_2 \leq 0.1$ wt %), based on the whole composition (including solvents when the composition of the present invention contains the following solvents).

The silicon-cobalt film forming composition of the present invention preferably further contains a solvent and is used in the form of a solution or a suspension.

The solvent usable for this purpose is not particularly limited as long as it dissolves or disperses the above silicon compound, the above cobalt compound and other components which are contained as required and does not react with these components. Preferred examples of such a solvent include a hydrocarbon-based solvent and an ether-based solvent.

Specific examples of the hydrocarbon-based solvent include n-pentane, cyclopentane, n-hexane, cyclohexane, n-heptane, cycloheptane, n-octane, cyclooctane, decane, cyclodecane, dicyclopentadiene hydride, benzene, toluene, xylene, durene, indene, tetrahydronaphthalene, decahydronaphthalene, and squalane. Specific examples of the ether-based solvent include diethyl ether, dipropyl ether, dibutyl ether, ethylene glycol dimethyl ether, ethylene glycol diethyl ether, ethylene glycol methylethyl ether, diethylene glycol dimethyl ether, diethylene glycol diethyl ether, diethylene glycol methylethyl ether, tetrahydrofuran, tetrahydropyran, and p-dioxane. These solvents (a types) can be used alone (a=1) or in admixture of two or more (a$\geq$2).

Of these, the hydrocarbon-based solvent or a mixture of the hydrocarbon-based solvent and the ether-based solvent is preferably used from the viewpoints of the solubility of the above silicon compound and cobalt compound and the stability of the composition to be obtained.

When the silicon-cobalt film forming composition of the present invention contains a solvent, the solvent is used in such an amount that the quantity of solids in the composition (i.e., the total quantity of the composition excluding the solvent) is preferably 0.1 to 50 wt %, more preferably 1 to 30 wt % of the whole composition.

The silicon-cobalt film forming composition of the present invention can be irradiated with light before applied on a substrate. Thereby, an increase in the molecular weight of the silicon compound to a high level occurs, and the coatability of the composition improves. The same effect is still achieved even when the silicon compound alone is irradiated with light in advance before the silicon compound is compounded with the cobalt compound. As the light to be irradiated, visible light, ultraviolet radiation, far-ultraviolet radiation, discharge light of a low-pressure or high-pressure mercury lamp, a deuterium lamp or a noble gas such as argon, krypton or xenon, a YAG laser, an argon laser, a carbon dioxide gas laser, or an excimer laser of XeF, XeCl, XeBr, KrF, KrCl, ArF or ArCl can be used. As these light sources, those with an output of 10 to 5,000 W are preferably used. In general, an output of 100 to 1,000 W is sufficient. Although the wavelength of these light sources is not particularly limited as long as the silane compound as a raw material can absorb it, it is preferably 170 to 600 nm.

The temperature ($T_1$) in the light irradiation treatment preferably ranges from room temperature to 300° C. ($T_1 \leq 300°$ C.). The treatment time is about 0.1 to 30 minutes. The light irradiation treatment is preferably carried out in a non-oxidizing atmosphere.

Method for Forming Silicon-Cobalt Film

The thus obtained silicon-cobalt film forming composition of the present invention is applied on a substrate to form a coating film of the composition. The material and shape of the substrate are not particularly limited. The material of the substrate is preferably a material which can endure a heat treatment temperature when the heat treatment is carried out in the subsequent step. Further, the substrate on which the coating film is formed may have an even surface or an uneven surface, and the form thereof is not particularly limited. Illustrative examples of the material of the substrate include glass, metal, plastic, and ceramic. As the glass, silica glass, borosilicate glass, soda glass or lead glass can be used, for example. As the metal, gold, silver, copper, nickel, silicon, aluminum, iron or stainless steel can be used. As the plastic, a polyimide or a polyether sulfone can be used, for example. The shape of these materials may be blocky, platy or filmy and is not particularly limited.

A method for applying the above composition is not particularly limited. Illustrative examples of the method include spin coating, dip coating, curtain coating, roll coating, spray coating, ink-jet coating, and printing. The composition may be applied only once or more than once.

The coating film may be formed to a desired thickness according to applications of the silicon-cobalt film to be formed. For example, when it is used for a semiconductor, the thickness of the coating film may be preferably 10 to 100 nm, more preferably 20 to 60 nm, and when it is used for conductive wiring, the thickness of the coating film may be preferably 100 to 5,000 nm, more preferably 500 to 3,000 nm.

When the silicon-cobalt film forming composition contains a solvent, the above thickness should be understood as the thickness after removal of the solvent.

The substrate used in the present invention can also be used as a substrate having both a hydrophobic portion and a hydrophilic portion on the same surface. Thereby, it becomes possible to form the coating film only in a specific portion on the substrate.

The hydrophobic portion of the substrate having both a hydrophobic portion and a hydrophilic portion on the same surface which is used in the present invention is formed by, for instance, applying a solution comprising hexamethylsilazane and the above fluorine-based surfactant to only a portion which will become the hydrophobic portion and then heating the coated substrate at 100 to 500° C. To apply the above solution to only the portion which will become the hydrophobic portion, the entire surface of the substrate is treated to become hydrophilic in advance as will be described later, the desired hydrophilic portion is covered, and the portion to become the hydrophobic portion is then treated to become hydrophobic. A method for covering the hydrophilic portion is not particularly limited. For instance, a method is used that comprises covering the portion which will not become the hydrophobic portion by a method of carrying out patterning in accordance with a known photolithographic method to cover the portion which will not become the hydrophobic portion with known resist or with a masking tape, forming a coating film of the composition of the present invention in the portion which will become the hydrophobic portion and then removing the resist or masking tape used in accordance with a known method. Further, it is also possible that a specific portion is treated to become hydrophilic after the entire surface of the substrate is treated to become hydrophobic in accordance with methods same as above.

Then, the thus obtained coating film of the silicon-cobalt film forming composition of the present invention is subjected to a heat treatment and/or a light treatment to be converted into a silicon-cobalt film.

The temperature ($T_2$) in the heat treatment is preferably 100° C. or higher ($T_2 \geq 100°$ C.), more preferably 150 to 500° C. The heating time is about 30 seconds to 120 minutes. Further, the atmosphere for carrying out the heat treatment is preferably an atmosphere which contains hydrogen and as least oxygen as possible, so that a good coating film can be obtained by baking the coating film in the atmosphere. Hydrogen in the above atmosphere for the heat treatment may be used as a mixed gas with, for example, nitrogen, helium or argon.

Alternatively, the coating film of the silicon-cobalt film forming composition can be irradiated with light to form the silicon-cobalt film. For the light treatment, discharge light of a low-pressure or high-pressure mercury lamp, a deuterium lamp or a noble gas such as argon, krypton or xenon, a YAG laser, an argon laser, a carbon dioxide gas laser, or an excimer laser of XeF, XeCl, XeBr, KrF, KrCl, ArF or ArCl can be used as a light source. As these light sources, those with an output of 10 to 5,000 W are generally used. In general, an output of 100 to 1,000 W is satisfactory. Although the wavelength of these light sources is not particularly limited, it is generally 170 to 600 nm. Further, use of a laser beam is particularly preferred from the viewpoint of the quality of the silicon-cobalt film to be formed. The temperature in irradiating the coating film with the light generally ranges from room temperature to 200° C. Further, only a specific portion may be irradiated with the light via a mask.

Silicon-Cobalt Film

The thus obtained silicon-cobalt film shows a metallic quality and may have a thickness suited for a particular application thereof. For example, when it is used for a semiconductor, the thickness may be preferably 5 to 1,000 nm, more preferably 30 to 500 nm, and when it is used as a conductive film for wiring, the thickness may be preferably 50 to 5,000 nm, more preferably 100 to 3,000 nm.

The thus obtained silicon-cobalt film of the present invention has a Co/Si atomic ratio which reflects the atomic ratio between Co and Si in the silicon-cobalt film forming composition and shows electric properties according to the ratio. For example, a silicon-cobalt film showing given electroconductivity is obtained by setting the Co/Si atomic ratio at about 0.1 to 10. For example, when the silicon-cobalt film is formed on the surface of a silicon layer to avoid formation of an ohmic contact in a semiconductor device, the Co/Si atomic ratio can be set at about 0.5.

The silicon-cobalt film of the present invention can be suitably used for electric circuits in a number of electronic devices including a semiconductor.

EXAMPLES

Hereinafter, the present invention will be further described with reference to Examples.

Example 1

In a nitrogen atmosphere, a mixed solution of 2.0 g of 20% toluene solution of cyclopentasilane and 1.2 g of 20% toluene solution of cyclopentadienyl dicarbonyl cobalt was irradiated with ultraviolet radiation (365 nm, 50 mW/cm$^2$) for 10 minutes by use of a high-pressure mercury lamp. Then, the solution was filtered by use of a polytetrafluoroethylene (PTFE) filter having apertures of 0.1 µm in size to prepare a coating solution. This coating solution was spin-coated on a quartz substrate at 1,000 rpm and then heat-treated at 100° C. for 5 minutes and then at 400° C. for 30 minutes to give a thin film having metallic luster. When the thickness of the thin film was measured by αstep (product of Tenchor Co., Ltd.), it was 150 nm. When this film was analyzed by ESCA, only Co and Si were detected, and the intensity ratio thereof was 1:2. The ESCA spectrum is shown in FIG. 1. Further, when the specific resistance of this film was measured in accordance with a four-terminal method, it was 21 µΩcm.

Example 2

A coating solution was prepared in the same manner as in Example 1 except that 1.3 g of bis(cyclopentadienyl)cobalt was used in place of cyclopentadienyl dicarbonyl cobalt. This coating solution was dip-coated on a quartz substrate. After prebaked on a hot plate of 100° C. for 10 minutes, the substrate was further heat-treated at 500° C. to obtain a film having a thickness of 3.2 µm and metallic luster. When this film was subjected to ESCA analysis, only Co and Si were detected, and the intensity ratio thereof was 1:2. When the specific resistance of this film was measured in accordance with a four-terminal method, it was 32 µΩcm.

Example 3

A coating solution was prepared in the same manner as in Example 1 except that dodecylbenzene was used as a solvent in place of toluene. This coating solution was linearly pattern-coated on a quartz substrate by an ink-jet method and then heat-treated on a hot plate at 400° C. for 1 hour to form a linear pattern having metallic luster and a thickness of 0.2 µm. The sheet resistance of the pattern was 160 Ω/□.

Example 4

A coating solution was prepared in the same manner as in Example 1 except that 1.6 g of octacarbonyl dicobalt was used in place of cyclopentadienyl dicarbonyl cobalt. The solution was filtered by a PTFE filter having apertures of 0.1 μm in size to prepare a coating solution. This coating solution was spin-coated on a quartz substrate at 1,000 rpm and then heat-treated at 100° C. for 5 minutes and then at 400° C. for 30 minutes to give a thin film having metallic luster. When this film was analyzed by ESCA, only Co and Si were detected, and the intensity ratio thereof was 1:2. When the specific resistance of this film was measured in accordance with a four-terminal method, it was 27 μΩcm.

Example 5

In a nitrogen atmosphere, cyclopentasilane was irradiated with ultraviolet radiation (365 nm, 50 mW/cm²) for 5 minutes by use of a high-pressure mercury lamp. Then, a 20% toluene solution was prepared. Then, a mixed solution of 2.0 g of this solution and 1.2 g of 20% toluene solution of cyclopentadienyl dicarbonyl cobalt was filtered by a PTFE filter having apertures of 0.1 μm in size to prepare a coating solution. This coating solution was spin-coated on a quartz substrate at 1,000 rpm and then heat-treated at 100° C. for 5 minutes and then at 400° C. for 30 minutes to give a thin film having metallic luster and a thickness of 150 nm. When this film was analyzed by ESCA, only Co and Si were detected, and the intensity ratio thereof was 1:2. When the specific resistance of this film was measured in accordance with a four-terminal method, it was 18 μΩcm.

Example 6

In a nitrogen atmosphere, cyclopentasilane was irradiated with ultraviolet radiation (365 nm, 50 mW/cm²) for 5 minutes by use of a high-pressure mercury lamp. Then, a 20% toluene solution was prepared. Then, a mixed solution of 2.0 g of this solution and 1.2 g of 20% toluene solution of cyclopentadienyl dicarbonyl cobalt was filtered by a PTFE filter having apertures of 0.1 μm in size to prepare a coating solution. This coating solution was spin-coated on a quartz substrate at 1,000 rpm and then heat-treated at 100° C. for 5 minutes and then at 400° C. for 30 minutes to give a thin film having metallic luster. This film was spin-coated with the filtered coating solution and heated under the same conditions to give a thin film having a thickness of 290 nm. When this film was analyzed by ESCA, only Co and Si were detected, and the intensity ratio thereof was 1:2. When the specific resistance of this film was measured in accordance with a four-terminal method, it was 42 μΩcm.

As described above, according to the present invention, there are provided a composition for forming a silicon-cobalt film easily at low production costs without expensive vacuum equipment and high-frequency generator, a method for forming a silicon-cobalt film by use of the composition, and a silicon-cobalt film formed by the method. The electric properties of the silicon-cobalt film formed by the method of the present invention can be controlled arbitrarily from a semiconductor field to a conductive field, and the silicon-cobalt film can be suitably used for solar batteries and various electric circuits.

The invention claimed is:

1. A method for forming a silicon-cobalt film which comprises:
forming a coating film of a silicon-cobalt film forming composition comprising a silicon compound and a cobalt compound on a substrate and subjecting the film to a heat treatment and/or a light treatment to form a silicon-cobalt film having a Co/Si atomic ratio of 0.1 to 10.

2. The method of claim 1, wherein the silicon compound is at least one compound selected from the group consisting of compounds represented by the following formulae (1a) to (1d):

$$Si_iX_{2i+2} \tag{1a}$$

(wherein X is a hydrogen atom, a halogen atom or a monovalent organic group, and i is an integer of 2 or larger), $$Si_jX_{2j} \tag{1b}$$

(wherein X is a hydrogen atom, a halogen atom or a monovalent organic group, and j is an integer of 3 or larger), $$Si_mX_{2m-2} \tag{1c}$$

(wherein X is a hydrogen atom, a halogen atom or a monovalent organic group, and m is an integer of 4 or larger), $$Si_kX_k \tag{1d}$$

(wherein X is a hydrogen atom, a halogen atom or a monovalent organic group, and k is 6, 8 or 10).

3. The method of claim 1, wherein the cobalt compound is a cobalt complex having at least either one of a CO ligand or a π ligand.

4. The method of claim 1, comprising subjecting the film to a heat treatment.

5. The method of claim 1, comprising subjecting the film to a light treatment.

6. The method of claim 1, comprising subjecting the film to a heat treatment and a light treatment.

7. The method of claim 1, comprising forming said coating film on a substrate and subjecting the film to a heat treatment and/or a light treatment to form a silicon-cobalt film having a Co/Si atomic ratio of 0.5.

8. The method of claim 2, wherein monovalent organic group represented by X in the formulae (1a), (1b), (1c) and (1d) is selected from the group consisting of an alkyl group having 1 to 12 carbon atoms, an alkenyl group having 2 to 12 carbon atoms, an alkynyl group having 2 to 12 carbon atoms, and an aromatic group having 6 to 12 carbon atoms.

9. The method of claim 8, wherein the silicon compound is a compound represented by formula (1a).

10. The method of claim 8, wherein the silicon compound is a compound represented by formula (1b).

11. The method of claim 8, wherein the silicon compound is a compound represented by formula (1c).

12. The method of claim 8, wherein the silicon compound is a compound represented by formula (1d).

13. The method of claim 1, wherein the silicon compound is at least one compound selected from the group consisting of n-pentasilane, iso-pentasilane, neo-pentasilane, n-hexasilane, n-heptasilane, n-octasilane, n-nonasilane, tetrachlorosilane, tetrabromosilane, hexachlorodisilane, hexabromodisilane, octachlorotrisilane octabromotrisilane, cyclotrisilane, cyclotetrasilane, cyclopentasilane, silylcyclotetrasilane, silylcyclotrisilane, silylcyclopentasilane, cyclohexasilane, heptasilane, cyclooctasilane, 1,1'-bicyclobutasilane, 1,1'-bicyclopentasilane, 1,1'-bicyclohexasilane, 1,1'-bicycloheptasilane, 1,1'-cyclobutasilylcyclopentasilane, 1,1'-cyclobutasilylcyclohexasilane, 1,1'-cyclobutasilylcycloheptasilane, 1,1'-cyclopentasilylcyclohexasilylsilane, 1,1'-cyclopentasilylcycloheptasilane, 1,1'-cyclohexasilylcycloheptasilane, spiro[2.2]pentasilane, spiro[3.3]heptasilane, spiro[4.4]nonasilane, spiro[4.5]decasilane, spiro[4.6]undecasilane, spiro[5.5]undecasilane, spiro[5.6]undecasilane, spiro[6.6]tridecasilane, hexasilaprismane and octasilacubane.

14. The method of claim 1, wherein the cobalt compound is at least one compound selected from the group consisting of $Co_3(CO)_{12}$, $Co_4(CO)_{12}$, cyclopentadienyl dicarbonyl cobalt, cyclopentadienyl carbonyl cobalt difluoride, cyclopentadienyl carbonyl cobalt dichloride, cyclopentadienyl carbonyl cobalt dibromide, cyclopentadienyl carbonyl cobalt diiodide, bis(cyclopentadienyl)cobalt, bis(cyclopentadienyl)carbonyl cobalt, bis(cyclopentadienyl)dicarbonyl cobalt, methyl cyclopentadienyl dicarbonyl cobalt, methyl cyclopentadienyl carbonyl cobalt difluoride, methyl cyclopentadienyl carbonyl cobalt dichloride, methyl cyclopentadienyl carbonyl cobalt dibromide, methyl cyclopentadienyl carbonyl cobalt diiodide, bis(methyl cyclopentadienyl)cobalt, bis(methyl cyclopentadienyl)carbonyl cobalt, bis(methyl cyclopentadienyl)dicarbonyl cobalt, tetramethyl cyclopentadienyl dicarbonyl cobalt, tetramethyl cyclopentadienyl carbonyl cobalt difluoride, tetramethyl cyclopentadienyl carbonyl cobalt dichloride, tetramethyl cyclopentadienyl carbonyl cobalt dibromide, tetramethyl cyclopentadienyl carbonyl cobalt diiodide, bis(tetramethyl cyclopentadienyl)cobalt, bis(tetramethyl cyclopentadienyl)carbonyl cobalt, bis(tetramethyl cyclopentadienyl)dicarbonyl cobalt, 1,5-cyclooctadiene dicarbonyl cobalt, 1,5-cyclooctadiene carbonyl cobalt difluoride, 1,5-cyclooctadiene carbonyl cobalt dichloride, 1,5-cyclooctadiene carbonyl cobalt dibromide, 1,5-cyclooctadiene carbonyl cobalt diiodide, bis(1,5-cyclooctadiene)cobalt, bis(1,5-cyclooctadiene)carbonyl cobalt, 1,3-cyclooctadiene dicarbonyl cobalt, 1,3-cyclooctadiene carbonyl cobalt difluoride, 1,3-cyclooctadiene carbonyl cobalt dichloride, 1,3-cyclooctadiene carbonyl cobalt dibromide, 1,3-cyclooctadiene carbonyl cobalt diiodide, bis(1,3-cyclooctadiene)cobalt, bis(1,3-cyclooctadiene)carbonyl cobalt, indenyl dicarbonyl cobalt, indenyl carbonyl cobalt difluoride, indenyl carbonyl cobalt dichloride, indenyl carbonyl cobalt dibromide, indenyl carbonyl cobalt diiodide, bis(indenyl)cobalt, bis(indenyl)carbonyl cobalt, $\eta^3$-allyl tricarbonyl cobalt, $\eta^3$-allyl carbonyl cobalt difluoride, $\eta^3$-allyl carbonyl cobalt dichloride, $\eta^3$-allyl carbonyl cobalt dibromide, $\eta^3$-allyl carbonyl cobalt diiodide, bis($\eta^3$-allyl)carbonyl cobalt, cyclopentadienyl(1,5-cyclooctadiene)cobalt, cyclopentadienyl(tetramethyl cyclopentadienyl)cobalt, tetramethyl cyclopentadienyl(1,5-cyclooctadiene)cobalt, cyclopentadienyl(methyl cyclopentadienyl)cobalt, methyl cyclopentadienyl(tetramethyl cyclopentadienyl)cobalt, methyl cyclopentadienyl(1,5-cyclooctadiene)cobalt, cyclopentadienyl(1,3-cyclooctadiene)cobalt, tetramethyl cyclopentadienyl(1,3-cyclooctadiene)cobalt, methyl cyclopentadienyl(1,3-cyclooctadiene)cobalt, cyclopentadienyl(cyclooctatetraenyl)cobalt, cyclopentadienyl(1,3-butadiene)cobalt, cyclopentadienyl(norbornadiene)cobalt, tetracarbonyl cobalt hydride, cyclopentadienyl carbonyl cobalt dihydride, methyl cyclopentadienyl carbonyl cobalt dihydride, tetramethyl cyclopentadienyl carbonyl cobalt dihydride, methyl tetracarbonyl cobalt, ethyl tetracarbonyl cobalt, bis(cyclopentadienyl)dicarbonyl cobalt, bis(tetramethyl cyclopentadienyl)dicarbonyl dicobalt, octacarbonyl dicobalt, (norbornene)hexacarbonyl dicobalt, cyclooctene hexacarbonyl dicobalt, bis(cyclopentadienyl) dimethyl dicarbonyl dicobalt, tetra($\eta^3$-allyl)dicobalt diiodide, bis(1,3-cyclohexadienyl)tetracarbonyl dicobalt, bis(norbornene)tetracarbonyl dicobalt, and bis(cyclopentadienyl)dicarbonyl dicobalt.

15. The method of claim 1, wherein the silicon compound is at least one compound selected from the group consisting of cyclopentasilane, silylcyclopentasilane, cyclotetrasilane, silylcyclotetrasilane, cyclotrisilane and silylcyclotrisilane and the cobalt compound is at least one compound selected from the group consisting of bis(cyclopentadienyl)cobalt, bis(tetracyclopentadienyl)cobalt, bis(1,3-cyclooctadienyl)cobalt, bis(1,5-cyclooctadiene)cobalt, bis(indenyl)cobalt, cyclopentadienyl dicarbonyl cobalt, methyl cyclopentadienyl dicarbonyl cobalt, tetramethyl cyclopentadienyl dicarbonyl cobalt, (1,3-cyclooctadiene)dicarbonyl cobalt, (1,5-cyclooctadiene)dicarbonyl cobalt, indenyl dicarbonyl cobalt, $\eta^3$-allyl tricarbonyl cobalt, cyclopentadienyl(1,3-cyclooctadiene)cobalt, cyclopentadienyl(1,5-cyclooctadiene)cobalt, cyclopentadienyl(indenyl)cobalt, indenyl(1,3-cyclooctadiene)cobalt, indenyl(1,5-cyclooctadiene)cobalt, and octacarbonyl dicobalt.

16. The method of claim 1, wherein the coating film has a thickness of 10 to 100 nm.

17. The method of claim 1, wherein the coating film has a thickness of 100 to 5,000 nm.

18. The method of claim 1, wherein the heat treatment is carried out at a temperature of 150 to 500° C. for 30 seconds to 120 minutes in an atmosphere comprising hydrogen and the light treatment is carried out with light having a wavelength of 170 to 600 nm.

19. The method of claim 1, wherein the silicon-cobalt film has a thickness of 5 to 1,000 nm.

20. The method of claim 1, wherein the silicon-cobalt film has a thickness of 50 to 5,000 nm.

* * * * *